(12) United States Patent
Toth et al.

(10) Patent No.: US 10,813,611 B2
(45) Date of Patent: Oct. 27, 2020

(54) METHOD OF PROCESSING FLUOROSCOPY IMAGES

(71) Applicant: Siemens Healthcare GmbH, Erlangen (DE)

(72) Inventors: Daniel Toth, Twickenham (GB); Peter Mountney, London (GB); Tanja Kurzendorfer, Trautmannshofen (DE); Christopher A. Rinaldi, London (GB); Kawal Rhode, Croydon (GB)

( * ) Notice: Subject to any disclaimer, the term of this patent is extended or adjusted under 35 U.S.C. 154(b) by 87 days.

(21) Appl. No.: 16/259,127

(22) Filed: Jan. 28, 2019

(65) Prior Publication Data

US 2019/0231289 A1    Aug. 1, 2019

(30) Foreign Application Priority Data

Jan. 30, 2018   (GB) .................................. 1801501.6
Jul. 24, 2018   (EP) ..................................... 18185243

(51) Int. Cl.
   *G06K 9/00*       (2006.01)
   *A61B 6/00*       (2006.01)
   (Continued)

(52) U.S. Cl.
   CPC ............... *A61B 6/487* (2013.01); *A61B 6/12* (2013.01); *A61B 6/484* (2013.01); *A61B 6/485* (2013.01);
   (Continued)

(58) Field of Classification Search
   CPC .......... A61B 6/032; A61B 6/12; A61B 6/463; A61B 6/481; A61B 6/484; A61B 6/485;
   (Continued)

(56) References Cited

U.S. PATENT DOCUMENTS

| | | | |
|---|---|---|---|
| 8,659,603 B2 * | 2/2014 | Song .................. | A61B 5/02007 345/440 |
| 2010/0254582 A1 * | 10/2010 | Liu ........................... | G06T 7/46 382/131 |

(Continued)

OTHER PUBLICATIONS

Behar, J. M. et. al.: "Comprehensive use of cardiac computed tomography to guide left ventricular lead placement in cardiac resynchronization therapy", in: Heart Rhythm, vol. 14, No. 9, pp. 1364-1372; Sep. 2017.

(Continued)

*Primary Examiner* — Gabriel I Garcia
(74) *Attorney, Agent, or Firm* — Lempia Summerfield Katz LLC (57) ABSTRACT

A method of extracting mechanical activation of the left ventricle from a sequence of contrasted X-ray fluoroscopy images is provided. The method includes: processing the image sequence to perform segmentation of the coronary veins; annotating branches of the segmented coronary veins; tracking the positions of the annotations throughout the fluoroscopy image sequence; computing the principle components of the motion of the annotations from the tracked positions; projecting the motion of the annotations to the axis corresponding to a first principle component; and analyzing the resulting motion curves to identify a latest activating region of the left ventricle.

14 Claims, 6 Drawing Sheets

(51) Int. Cl.
| | |
|---|---|
| G06T 7/00 | (2017.01) |
| G06T 7/246 | (2017.01) |
| A61B 6/12 | (2006.01) |
| A61N 1/362 | (2006.01) |
| A61B 90/00 | (2016.01) |
| A61B 6/03 | (2006.01) |

(52) U.S. Cl.
CPC .............. *A61B 6/504* (2013.01); *A61B 6/547* (2013.01); *G06T 7/0012* (2013.01); *G06T 7/246* (2017.01); *A61B 6/032* (2013.01); *A61B 6/463* (2013.01); *A61B 6/481* (2013.01); *A61B 2090/376* (2016.02); *A61N 1/3627* (2013.01); *G06K 2209/051* (2013.01); *G06T 2207/10016* (2013.01); *G06T 2207/10121* (2013.01); *G06T 2207/30048* (2013.01)

(58) Field of Classification Search
CPC ......... A61B 6/487; A61B 6/504; A61B 6/547; A61B 2090/376; G06T 7/0012; G06T 7/246; G06T 2207/10016; G06T 2207/10121; G06T 2207/30048; A61N 1/3627; G06K 2209/051
USPC ........................................................ 382/132
See application file for complete search history.

(56) References Cited

U.S. PATENT DOCUMENTS

| | | | | |
|---|---|---|---|---|
| 2010/0268059 | A1* | 10/2010 | Ryu | A61N 1/3627 600/407 |
| 2013/0116739 | A1* | 5/2013 | Brada | A61B 6/504 607/9 |
| 2017/0071675 | A1 | 3/2017 | Dawoud | |
| 2017/0337343 | A1* | 11/2017 | Kakadiaris | G06F 19/00 |
| 2020/0175679 | A1* | 6/2020 | Reiber | A61B 5/02 |

OTHER PUBLICATIONS

Claridge, Simon et al. "Effects of Epicardial and Endocardial Cardiac Resynchronization Therapy on Coronary Flow: Insights From Wave Intensity Analysis" Journal of the American Heart Association (JAHA), vol. 4, Issue 12, pp. 1-11; Dec. 23, 2015.
Daubert, J.-C. et. al.: "2012 EHRA/HRS expert consensus statement on cardiac resynchronization therapy in heart failure: implant and follow-up recommendations and management", in: Europace, vol. 14, No. 9, pp. 1236-1286, 2012.
Jolliffe, I.T. et al. "Principal Component Analysis" Springer, New York, pp. 1-487; 2002.
Jolly, M.-P., et al. "Automatic Segmentation of the Myocardium in Cine MR Images Using Deformable Registration" STACOM—Imaging and modelling intelligence, vol. 8896, pp. 1-10, 2011.
Kass, David A. "An Epidemic of Dyssynchrony" Journal of the American College of Cardiology (JACC), vol. 51, No. 1, pp. 12-17; Jan. 2008.
Khan, F. Z. et. al.: "Targeted Left Ventricular Lead Placement to Guide Cardiac Resynchronization Therapy", in: Journal of the American College of Cardiology, vol. 59, No. 17, pp. 1509-1518, 2012.
McAlister, Finlay A. et al. "Cardiac Resynchronization Therapy for Patients With Left Ventricular Systolic Dysfunction—A Systematic Review" JAMA, vol. 297, No. 22, pp. 2502-2514; Jun. 2007.
Mountney, P. et. al.: "A Planning and Guidance Platform for Cardiac Resynchronization Therapy", in: IEEE Transactions on Medical Imaging, vol. 36, No. 11, pp. 2366-2375; Nov. 2017.
Mozaffarian, D. et. al.: "Heart Disease and Stroke Statistics—2015 Update", in: Circulation, vol. 131, No. 4, pp. e29-e322, Jan. 2015.
Scarborough, Peter et al. "The economic burden of ill health due to diet, physical inactivity, smoking, alcohol and obesity in the UK: an update to Jul. 2006 NHS costs" Journal of Public Health, vol. 33, No. 4, pp. 527-535, May 11, 2011.
Spragg, David D. et al. "Pathobiology of Left Ventricular Dyssynchrony and Resynchronization" Progress in Cardiovascular Diseases, vol. 49, No. 1, pp. 26-41, Jul.-Aug. 2006.
European Search Report for European Patent Application No. 181852435-1207 dated Apr. 3, 2019.

* cited by examiner

METHOD OF PROCESSING FLUOROSCOPY IMAGES

The application claims the benefit of Great Britain Patent Application No. GB 1801501.6, filed Jan. 30, 2018, and European Patent Application No. EP 18185243.5, filed Jul. 24, 2018, which are hereby incorporated by reference in their entireties.

BACKGROUND

The disclosure describes a method of extracting mechanical activation of the left ventricle from a sequence of contrasted X-ray fluoroscopy images. The disclosure further describes an image processing arrangement, and a computer program product.

BACKGROUND

Cardiovascular disease (CVD) is the leading global cause of death and accounts for over 30% of deaths per year. CVD contributes to 42% of deaths in the EU. CVD is associated with significant morbidity and mortality as first line treatments are not always effective in improving symptoms and quality of life.

Congestive heart failure with dyssynchrony results in reduced function of the left ventricle as electrical impulses are delayed in transmission to the ventricles. In some patients, first-line pharmacological interventions are not always effective in improving symptoms and quality of life. Cardiac resynchronization therapy (CRT) has been shown to reduce mortality in patients with advanced drug-refractory heart failure, systolic dysfunction, chronic systolic heart failure, and ventricular dyssynchrony. This minimally invasive intervention may alleviate symptoms, increase ejection fraction, and shorten the electrocardiogram QRS duration. In spite of its advantages, CRT has a high non-response rate associated with sub-optimal left ventricle (LV) lead placement. This is because the presence of myocardium scar tissue in the position of the lead hinders the activation of the myocardium. Knowing where to place the LV lead is very challenging for operators performing the procedure as very little information is available to them during the procedure.

The coordinated contraction and expansion of the chambers of the heart are controlled by electrical systole and mechanical systole of the cardiac electrical conduction system. During electrical systole, electrical pulses travel through bundle branches of the myocardium. These signals trigger a response in the myocardial cells, resulting in muscular contraction or mechanical systole, with a certain timing between atrial and ventricular contractions. This biomechanical contraction of the myocardium is referred to as "mechanical activation." In a patient with heart disease, the myocardium may contract unevenly, e.g., the right ventricle may contract before the left ventricle because of left bundle branch block (LBBB). Scar tissue from an earlier infarct may also negatively affect the mechanical systole timing. It has been shown in several studies that positioning the LV lead in the latest-activating region of the myocardium may increase the likelihood of a positive response for CRT implants. However, the currently available procedures and equipment for identifying the latest-activating region of the myocardium are expensive. Cardiac magnetic resonance (CMR) imaging may detect scar tissue and interventricular dyssynchrony, thereby improving the outcome of CRT. However, this technique is expensive and not available in many clinical settings. Ultrasound speckle-tracking 2D radial strain imaging may be used to detect dyssynchrony in addition to identifying the latest activating segment, but requires a skilled operator. Computed tomography (CT), despite the radiation risks associated with patient exposure, may be utilized to calculate the latest mechanically activating segment for optimal lead position. These methods all require additional pre-operative imaging. For these reasons, it is not standard clinical practice to identify the latest-activating myocardial region in advance of a CRT procedure.

SUMMARY AND DESCRIPTION

It is therefore an object of the disclosure to provide an improved method of identifying the latest-activating region of the myocardium.

The scope of the present disclosure is defined solely by the appended claims and is not affected to any degree by the statements within this description. The present embodiments may obviate one or more of the drawbacks or limitations in the related art.

According to the disclosure, the method of extracting mechanical activation of the left ventricle from a sequence of contrasted X-ray fluoroscopy images includes the acts of: processing the image sequence to perform segmentation of the coronary veins; annotating branches of the segmented coronary veins; tracking the positions of the annotations throughout the fluoroscopy image sequence; computing the principle components of the motion of the annotations from the tracked positions; projecting the motion of the annotations to the axis corresponding to a first principle component; and analyzing the resulting motion curves to identify a latest activating region of the left ventricle.

In the method, venograms which may be acquired during the CRT procedure may be used to derive mechanical activation and identify the latest activating region of the LV. Each patient's coronary anatomy may be segmented from the venograms. These segmentations were then skeletonized and the branches of the coronary sinus (CS) were identified and tracked.

The present disclosure provides a method of extracting mechanical activation of the left ventricle from contrasted X-ray fluoroscopy, e.g., to deduce information about mechanical systole of the left ventricle using a sequence of contrasted X-ray fluoroscopy images. The method includes the segmentation of the coronary veins, annotating the branches of the veins, tracking the 2D positions of the annotated branches throughout the fluoroscopy sequence, computing the principle components of the motion of the labels, projecting the motion to the axis corresponding to the first principle component and analyzing the resulting motion curves. The motion is associated with the motion of the cardiac wall.

As explained above, mechanical activation is a term used to refer to mechanical systole, e.g., the contraction of the myocardium (with the left ventricle) in response to electrical systole. The method allows the mechanical activation to be identified or "extracted" from a sequence of contrasted X-ray fluoroscopy images. In such a sequence of images, the X-ray opaque contrast agent serves to make the blood vessels of the coronary sinus appear clearly in the X-ray images. A contrasted X-ray fluoroscopy may be performed prior to or during a CRT procedure to allow the operator to observe placement of the CRT leads, for example, leads of a bi-ventricular pacemaker. The disclosure is based on the insight that the coronary sinus lies on the epicardium, so that contraction/dilation of the underlying myocardium results in corresponding movement of the CS, resulting in slight displacements of the CS blood vessels in successive images of a contrasted X-ray fluoroscopy procedure. The mechanical systole timing may be extracted from such a sequence of images by tracking the movements of CS nodes or branches throughout the image sequence and applying a technique of principle component analysis (PCA) to the tracked motion data. With the method disclosed herein, no costly preoperative acquisition such as MRI or computed tomography is required, and there is no need for an ultrasound scan performed by a skilled operator. Furthermore, the success rate of unguided CRT interventions may be increased.

The method presents a novel way of estimating mechanical activation information by tracking the motion of CS vessels in venograms. The approach does not require additional pre-operative imaging and enables guided CRT lead placement using only intra-operative X-ray fluoroscopy imaging. It is significantly easier and more economical to perform X-ray fluoroscopy during the CRT intervention and to apply the PCA-based motion analysis of the annotated venous branches of the CS, instead of tracking the cardiac wall during an expensive MRI procedure.

The image processing arrangement for extracting left ventricle mechanical activation information from a sequence of cardiac contrasted X-ray fluoroscopy images includes: a segmentation module realized to perform segmentation of the coronary veins; an annotation module for annotating branches of the segmented coronary veins; a tracker module configured to track the positions of the annotations in the fluoroscopy image sequence; and a principle component analysis module for computing the principle components of the motion of the annotated branches and to present this information in the form of motion curves of the annotations.

The image processing arrangement is useful for a CRT suite in a clinic environment. The extracted information relating to mechanical activation of the left ventricle may guide CRT interventions so that these may be performed without preoperative imaging such as MRI. The image processing arrangement may therefore be deployed at any site that is equipped with a catheterization laboratory.

The computer program product includes a computer program that is directly loadable into a memory of a control unit of an embodiment of the image processing arrangement and includes program elements for performing acts of the method when the computer program is executed by the control unit of the image processing arrangement.

The disclosure describes a method to extract mechanical activation of the left ventricle from contrasted X-ray fluoroscopy, the method including the acts of: segmentation of the coronary veins; annotating branches of the veins; tracking 2D positions of the annotated branches throughout the fluoroscopy sequence; computing the principle components of the motion of the labels; projecting the motion to the axis corresponding to the first principle component; and analyzing the resulting motion curves.

In the following, without restricting the disclosure in any way, it may be assumed that the sequence of fluoroscopy images includes images obtained over at least one complete cardiac cycle. The sequence of fluoroscopy images may be obtained at a frame rate of at least 7.5 frames per second and/or at a resolution of at least 130 ms.

As indicated above, to compute the mechanical activation curves from X-ray images, a patient is subject to a contrast-enhanced fluoroscopy. Using known image processing techniques, the coronary veins are segmented in the images, e.g., the network of veins is identified and highlighted in the images. The resulting segmentation mask is then skeletonized (again, using known image processing techniques) to show the "skeleton" of the branches of the coronary sinus. The results of such image processing acts, (e.g., a segmentation mask, a skeletonization layer, etc.), may be presented to a user in a transparent layer overlaid on the original image. Any annotations or labels may be placed in a similar transparent layer, for example a layer that is overlaid on a skeletonization, or a layer that is overlaid on a fluoroscopy image, etc. The terms "annotation" and "label" may be regarded as synonyms and may be used interchangeably in the following.

As the coronary veins overlie the epicardium, the latest moving blood vessel of the CS will correlate to the latest activating segment of the myocardium. In one embodiment, the annotation module is realized to automatically identify a branch of the coronary veins and to place an annotation accordingly. The venous anatomy may vary from patient to patient, so that some of the great vessels of the left ventricle may not be completely visible in the images. However, it is sufficient to be able to identify one point on each potential target vein to place an LV lead. The act of annotating a branch of the CS includes placing a label on that branch in an image of the image sequence. A label may be placed at any position along a branch of the CS. However, in an embodiment, a label is placed at a vein bifurcation or node, because a bifurcation may be tracked more easily throughout the image sequence. In an initial annotation act, an image showing the set of labels and the CS may be displayed to a user for approval or adjustment of the proposed set of labels. The annotation module may be realized to permit manual placement of annotations. Of course, with suitable software, it would be possible to carry out the annotation in a completely automated manner. The labels are placed in all images of the image sequence. The motion of the labels is compared and a decision is made between the vessels.

In an embodiment, multiple CS branches are labelled accurately and numbered that each branch may be tracked throughout the frames of the cardiac cycle captured during the contrasted X-ray fluoroscopy procedure. At least two annotations or labels may be placed and tracked in the image sequence, whereby one label is placed at a suitable node in the target vein into which the operator wishes to place an LV lead. Of course, any number of annotations is possible, for example five, seven labels, etc.

Principle component analysis (PCA) is performed to calculate the characteristic axes of motion of the labelled branches in two dimensions, e.g., in the image plane. The three-dimensional movement resulting from mechanical activation of the myocardium will result in slight displacements of the labels in the two-dimensional image plane. Therefore, between any two images in the image sequence (e.g., assuming a suitably fine image resolution and a suitable frame rate), some slight displacement will be observed in several or all. The 3D movement of the myocardium will therefore "translate" into 2D pixel displacements of the labels in the image sequence.

The question of relevance to the operator is which myocardial region is last to activate, e.g., the myocardial region delayed the most. This question may be answered by applying PCA to analyze the tracked label positions as follows. The main principle component is associated with cardiac motion. The motion of the labelled branches, (e.g., the pixel displacements of the labels), is projected onto the axis corresponding to the main principle component, (e.g., the Y-axis), and the displacement of each label is tracked over time, (e.g., in each of the sequence of images). By plotting the pixel displacements of each label over time, this motion is visualized throughout the cardiac cycle.

The myocardium contracts and dilates during a complete cardiac cycle, so that each label (e.g., a point on the CS) is expected to move "outwards" during dilation of the myocardium, and to move "inwards" during contraction. In a patient with cardiac disease such as dyssnychrony, the ventricles may contract with significant delay. With this insight, the points of contraction may be located by assessing the timing of the minima of the motion curves for the annotated CS branches. The minima—which define the points of myocardial contraction—are identified and their relative delay is measured. The "latest" minimum (e.g., the most delayed minimum) identifies the vessel to be targeted during CRT delivery. By analysis of these features, it is possible to estimate the mechanism of contraction for each region of the myocardium under a labelled CS branch, and any delay between labels may provide valuable information regarding any myocardial dyssynchrony.

As an alternative approach, a strain measure may be computed by investigating the relative motion of branches. In other words, any relative movement between two branches may be observed and interpreted, for example, to identify akinetic vessel segments, and any underlying akinetic myocardium.

BRIEF DESCRIPTION OF THE DRAWINGS

Other objects and features of the present disclosure will become apparent from the following detailed descriptions considered in conjunction with the accompanying drawings. It is to be understood, however, that the drawings are designed solely for the purposes of illustration and not as a definition of the limits of the disclosure.

In the diagrams, like numbers refer to like objects throughout. Objects in the diagrams are not necessarily drawn to scale.

DETAILED DESCRIPTION

Figure 1:
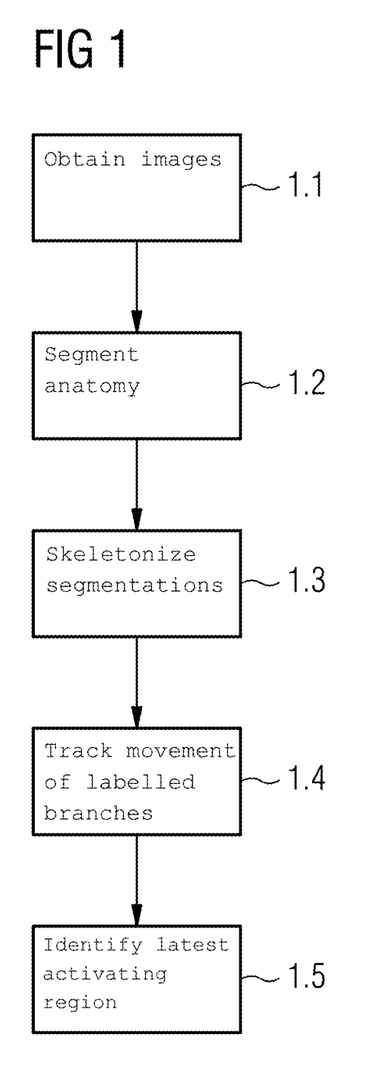
FIG. 1 depicts acts in a workflow in an embodiment of the method.
Figure 2:
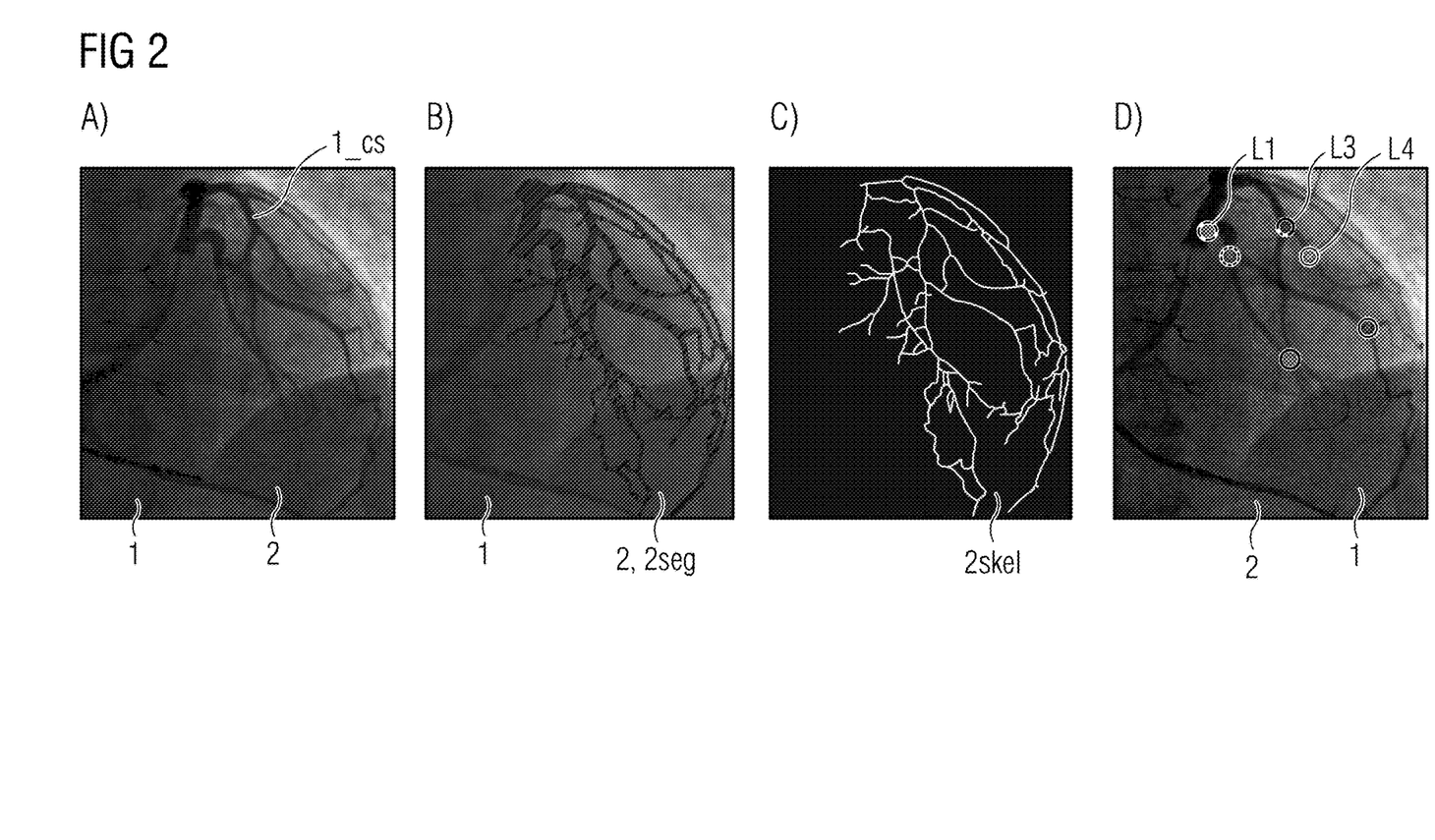
FIG. 2 depicts image processing stages in the workflow of FIG. 1, according to an embodiment.
Figure 3:
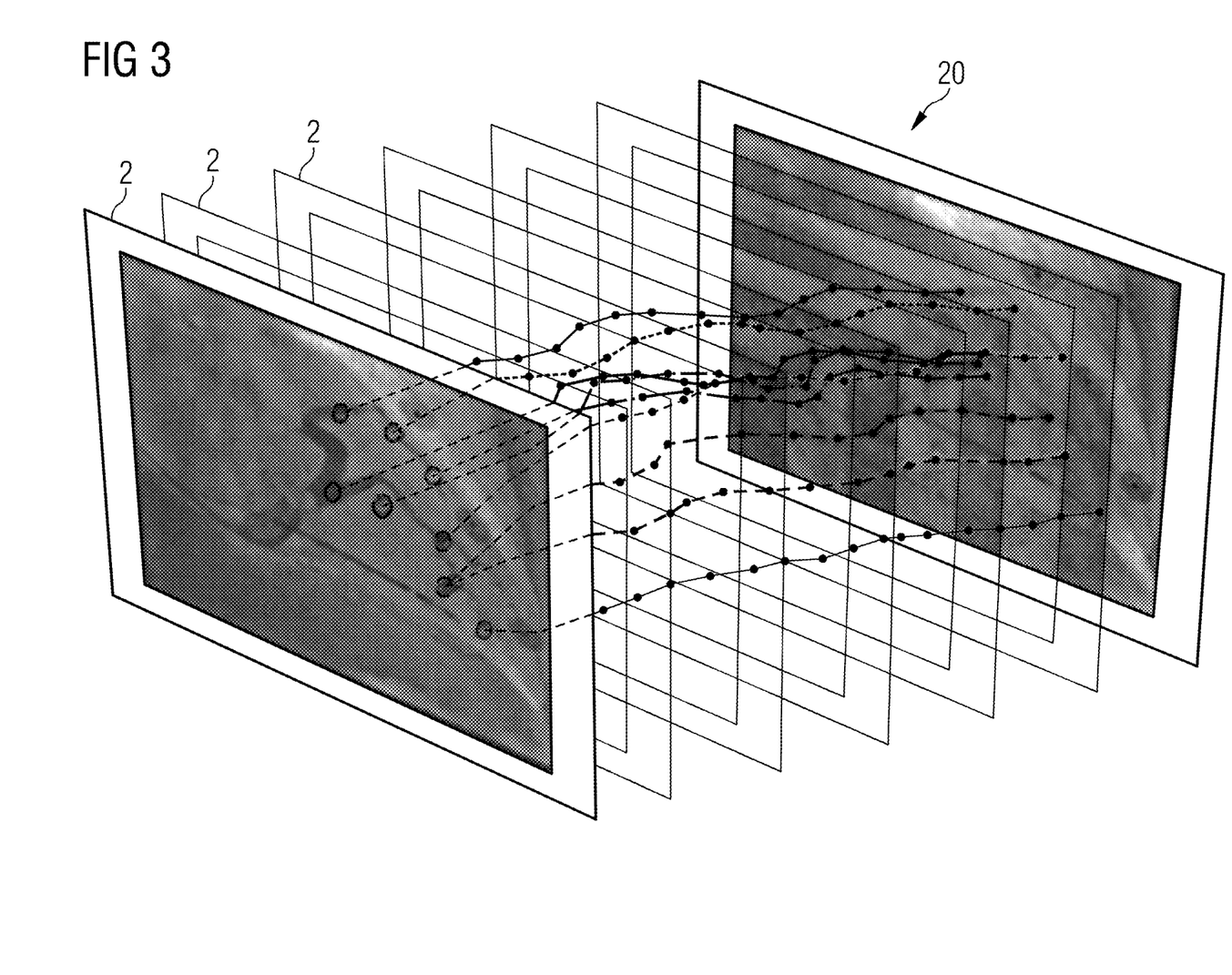
FIG. 3 illustrates the tracking of annotations in a sequence of images, according to an embodiment.

An example of the method will now be described. FIG. 1 illustrates a workflow to compute mechanical activation from X-ray fluoroscopy images, while FIG. 2 depicts image processing acts carried out on an exemplary venogram image obtained during the cardiac cycle. In act 1.1 of FIG. 1, fluoroscopy images 2 or venograms are obtained during an angiography. Part of an exemplary image 2 of such a sequence is shown on the left in FIG. 2, and indicates the network of vessels collectively referred to as the coronary sinus 1_CS. Fluoroscopic sequences may be acquired with the whole heart and its movement for at least one cardiac cycle so that a successful segmentation and annotation of the scan may be achieved. A fluoroscopic sequence 20 as shown in FIG. 3 may be acquired at a suitable frame rate and temporal resolution, (e.g., a frame rate of 7.5 frames per second at a temporal resolution of 133 ms, a frame rate of 15 frames per second at a temporal resolution of 67 ms, etc.)

The patient's coronary anatomy was segmented from the venograms in act 1.2. In the segmentation, the coronary veins 1_CS are identified and extracted from the X-ray images, as indicated in part B of FIG. 2, which shows a segmentation layer 2seg overlaid on the image 2. These segmentations were then skeletonized in act 1.3 of FIG. 1. Segmentation and skeletonization are performed for multiple images in the sequence, and exemplary results are shown in part C of FIG. 2, which shows a skeletonization layer 2skel. The skeletonization layer 2skel is used to identify the locations of suitable labels L1, . . . , L6 shown in part D of FIG. 2.

As shown in part D of FIG. 2, the labels L1, . . . , L6 are placed at suitable points along the branches of the blood vessels, for example, at bifurcations of the coronary sinus 1_CS. The labels L1, . . . , L6 are used in the subsequent tracking act given as act 1.4 in FIG. 1. Principle Component Analysis (PCA) is used to track the movement of the labelled branches throughout the cardiac cycle, e.g., the movements of the branches are tracked throughout the image sequence. FIG. 3 depicts a sequence 20 of venogram images 2 generated during a cardiac cycle, illustrating the tracking of bifurcations through the cardiac cycle. The lines connecting the images represent the movement of the labels over time. The foremost image 2 on the left indicates ten labels. In act 1.5, mechanical activation is derived from the tracked points by analyzing their motion using PCA.

Figure 4:
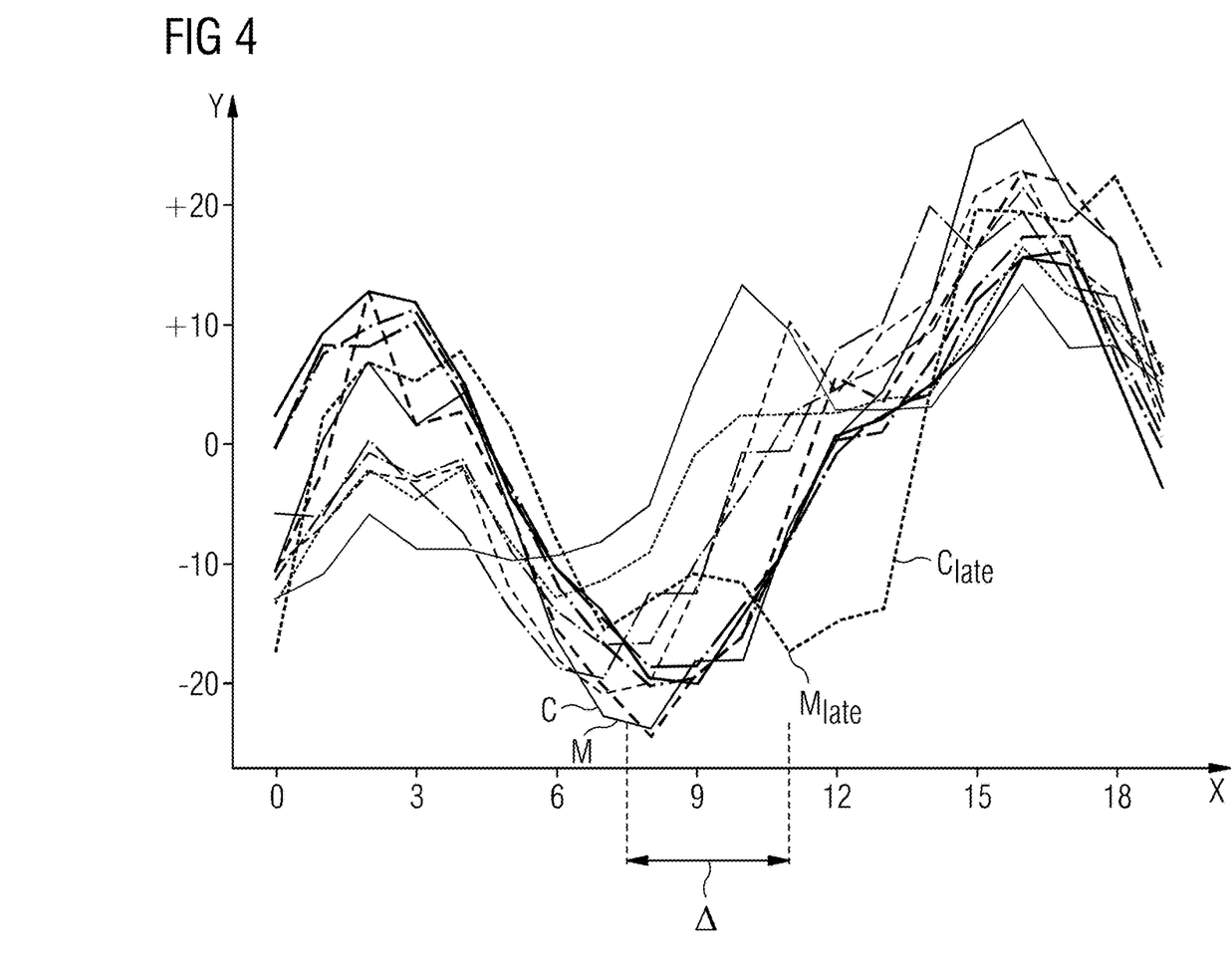
FIG. 4 depicts a number of motion curves obtained using an embodiment of the method.

Mechanical activation curves may then be computed for each branch of the skeletonized CS. FIG. 4 depicts an exemplary set of curves obtained by tracking the positions of ten labels over a complete cardiac cycle. The graph shows pixel displacement (Y-axis) against frame count (X-axis). In this example, curve C is identified as the primary motion curve, e.g., the motion curve corresponding to a label placed on a major vessel of the CS. The curve $C_{late}$ exhibits a distinct lag or delay $\Delta$ relative to the other curves, indicating that the corresponding branch of the CS is closest to the latest-activating myocardium region and would be the most suitable position for the LV lead that will be placed during the CRT procedure.

An alternative method to compute mechanical activation from X-ray fluoroscopy is to measure the relative position of two labelled branches throughout the cardiac cycle. However, strain measurements may mistake normal or synchronous contraction of the myocardium as akinetic when two labels are close together. Temporal resolution cannot distinguish between the two different events.

Figure 5:
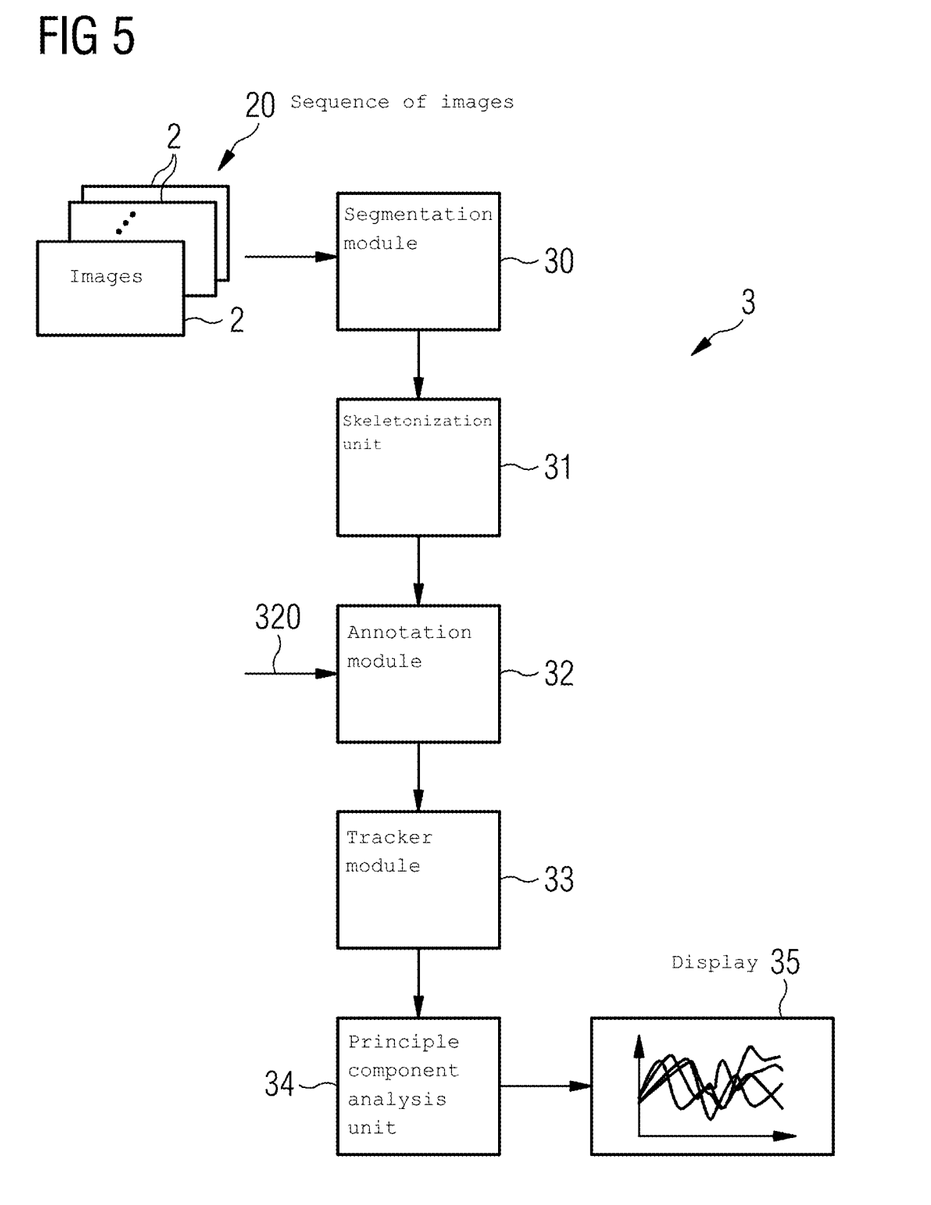
FIG. 5 depicts an embodiment of the image processing arrangement.

FIG. 5 depicts an exemplary image processing arrangement 3 for extracting left ventricle mechanical activation information from a sequence 20 of contrasted X-ray fluoroscopy images 2, which may be obtained during a guided or unguided CRT procedure, for example. The image processing arrangement 3 includes a segmentation module 30 for performing segmentation of the coronary veins 1_CS in the images 2. The segmented CS may then be skeletonized in a suitable skeletonization unit 31. Subsequently, suitable bifurcations, branches, or nodes of the CS may be automatically and/or manually identified as candidate points to track throughout the image sequence 20, and these points may be assigned labels or annotations by an annotation module 32. Manual input 320 is indicated, for example, to approve and/or edit a set of annotations. A tracker module 33 identifies the position of each label in each image, and computes any deviation (e.g., in pixels) relative to the position of that label in the preceding image. This information is passed to a principle component analysis unit 34 that computes the principle components of the motion of the annotations. The results of the PCA are plotted as motion curves for each label, and the motion curves are presented to a user, for example, on a display 35. The user or operator may then identify the most suitable region of the CS into which to place the LV lead in the CRT procedure.

Figure 6:
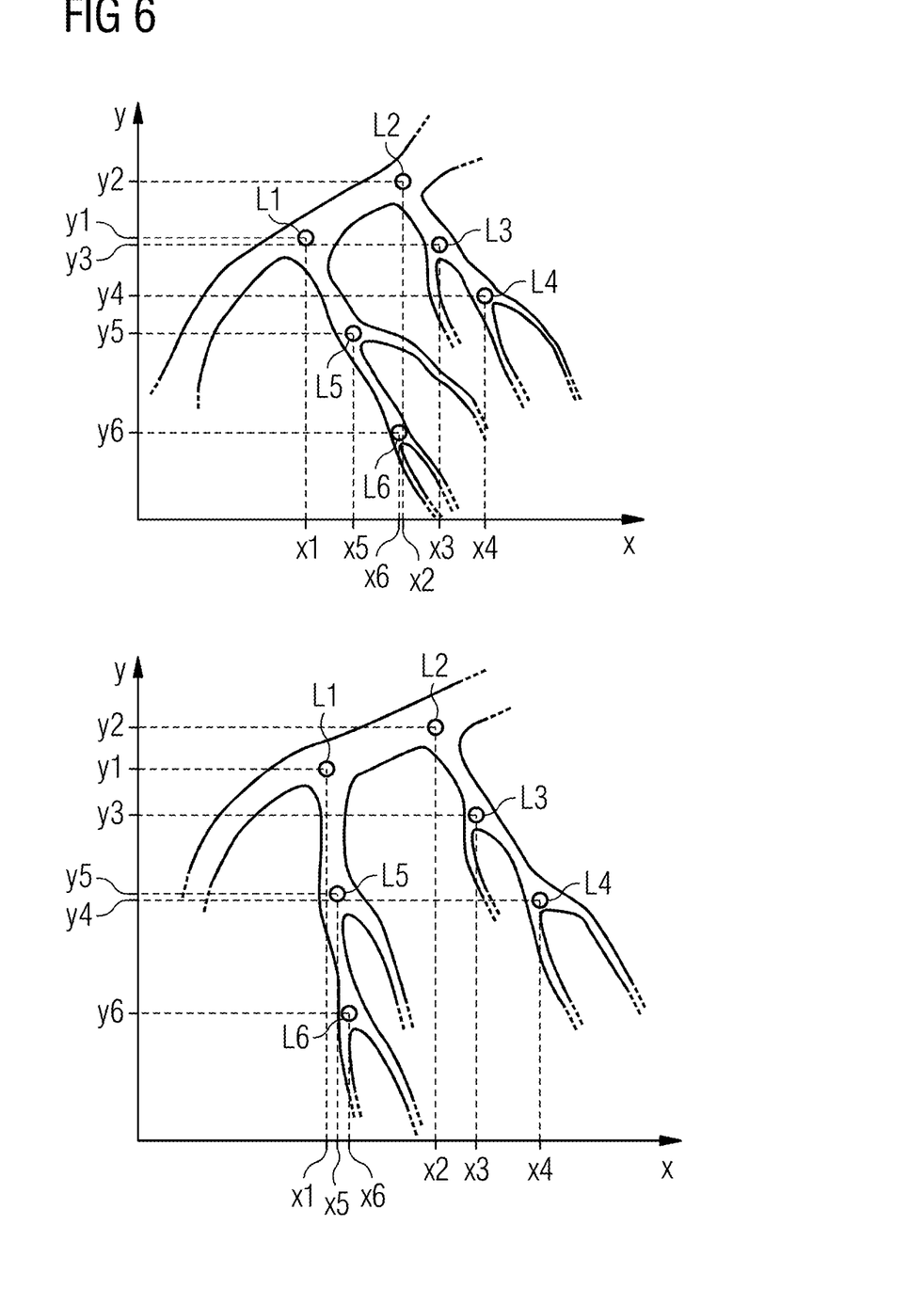
FIG. 6 illustrates position tracking as implemented in an embodiment of the method.

FIG. 6 illustrates the underlying principle of the method. A part of the annotated CS is shown relative to X and Y axes of an image plane. The diagram shows six labels L1, ..., L6 placed at suitable points, for example, at points identified with the help of a skeletonized layer following a segmentation act. It may suffice to place two labels, e.g., label L3/L6 and label L3/L4, if an LV lead is to be placed into one or both of these branches of the CS. Each label L1, ..., L6 is a point or pixel in the image, and may be defined by a coordinate pair as indicated by the X-coordinates x1, ..., x4 and Y-coordinates y1, ..., y6. During a cardiac cycle, the myocardium contracts and expands. The movement of the myocardial regions may be deduced by tracking the coordinates of the labels, e.g., by measuring any pixel offsets from one image to the next. In this example, the myocardium is undergoing expansion from the upper diagram to the lower diagram, and the coordinates of each label L1, ..., L6 alter accordingly. The X-offsets and Y-offsets of the labels in the images of the image sequence may be counted in pixels or any other appropriate unit, and fed to the PCA module which performs principle component analysis to estimate motion curves for each label.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method of extracting mechanical activation of a left ventricle from an image sequence of contrasted X-ray fluoroscopy images, the method comprising:
processing the image sequence to perform a segmentation of coronary veins within the fluoroscopy images;
annotating branches of the segmented coronary veins;
tracking positions of the annotations throughout the image sequence;
computing principle components of a motion of the annotations from the tracked positions;
projecting the motion of the annotations to an axis corresponding to a first principle component;
analyzing resulting motion curves to identify a latest activating region of the left ventricle; and
identifying a primary motion curve associated with a main vein of a coronary sinus.

2. The method of claim 1, wherein a position of an annotation is noted in an initial image of the image sequence, and
wherein the motion of an annotation is tracked by determining the position of the annotation from the initial image in remaining images of the image sequence.

3. The method of claim 1, further comprising:
identifying minima in the motion curves; and
measuring a relative delay between the minima, wherein the delay of a motion curve minimum is measured relative to a corresponding minimum of the primary motion curve.

4. The method according to claim 3, further comprising:
identifying a motion curve with a largest relative delay; and
identifying a corresponding annotated branch of the coronary veins to identify a late-activating region of the left ventricle.

5. The method of claim 1, wherein the annotating of the branches comprises placing a label on a respective branch in a segmented and/or skeletonized layer superposed on an image of the image sequence.

6. The method of claim 5, wherein a label is placed at a vein bifurcation.

7. The method of claim 1, wherein at least two annotations are tracked in the image sequence.

8. The method of claim 1, wherein the image sequence is obtained at a frame rate of at least 7.5 frames per second, at a resolution of at least 130 ms, or a combination thereof.

9. The method of claim 1, wherein the image sequence comprises images obtained over at least one complete cardiac cycle.

10. An image processing arrangement for extracting left ventricle mechanical activation information from an image sequence of contrasted X-ray fluoroscopy images, the image processing arrangement comprising:
a control unit configured to:
perform a segmentation of coronary veins;
annotate branches of the segmented coronary veins;
track positions of the annotations in the image sequence;
compute principle components of motion of the annotated branches;
provide motion curves of the annotations representing the computed principle components; and
identify a primary motion curve associated with a main vein of a coronary sinus.

11. The image processing arrangement of claim 10, wherein the control unit is configured to automatically identify a branch of the coronary veins and to place an annotation accordingly.

12. The image processing arrangement of claim 10, wherein the control unit is configured to replicate the annotations in a plurality of images of the image sequence.

13. The image processing arrangement of claim 10, wherein the image processing arrangement is configured to allow manual image annotation.

14. A non-transitory computer program product comprising a computer program configured to be directly loadable into a memory of a control unit of an image processing arrangement and which comprises program elements, wherein, when the computer program is executed by the control unit of the image processing arrangement, causes the control unit to:
segment coronary veins within an image sequence of contrasted X-ray fluoroscopy images;
annotate branches of the segmented coronary veins;

track positions of the annotations throughout the image sequence;
compute principle components of a motion of the annotations from the tracked positions;
project the motion of the annotations to an axis corresponding to a first principle component;
analyze resulting motion curves to identify a latest activating region of a left ventricle; and
identify a primary motion curve associated with a main vein of a coronary sinus.

* * * * *